United States Patent
Dalmases Barjoan et al.

(10) Patent No.: US 7,759,484 B2
(45) Date of Patent: Jul. 20, 2010

(54) MIXED SOLVATE OF OLANZAPINE, METHOD FOR PREPARING IT AND METHOD FOR PREPARING FORM I OF OLANZAPINE THEREFROM

(75) Inventors: Pere Dalmases Barjoan, Sant Feliu de Llobregat (ES); Jordi Bessa Bellmunt, Barcelona (ES)

(73) Assignee: Inke, S.A., Castellbisbal (ES)

( * ) Notice: Subject to any disclaimer, the term of this patent is extended or adjusted under 35 U.S.C. 154(b) by 693 days.

(21) Appl. No.: 11/568,021

(22) PCT Filed: Jul. 7, 2005

(86) PCT No.: PCT/IB2005/002209

§ 371 (c)(1), (2), (4) Date: Oct. 17, 2006

(87) PCT Pub. No.: WO2006/013435

PCT Pub. Date: Feb. 9, 2006

(65) Prior Publication Data

US 2008/0280884 A1    Nov. 13, 2008

(30) Foreign Application Priority Data

Jul. 27, 2004    (ES) ................. 200401850

(51) Int. Cl.
*C07D 495/04*    (2006.01)
(52) U.S. Cl. ..................................... 540/557
(58) Field of Classification Search ............ 540/557
See application file for complete search history.

(56) References Cited

U.S. PATENT DOCUMENTS

| | | | |
|---|---|---|---|
| 5,631,250 A | 5/1997 | Bunnell et al. | |
| 5,637,584 A | 6/1997 | Larsen | |
| 5,703,232 A | 12/1997 | Bunnell et al. | |

FOREIGN PATENT DOCUMENTS

| | | |
|---|---|---|
| EP | 0 454 436 A1 | 10/1991 |
| EP | 0 733 634 A1 | 9/1996 |
| EP | 0 733 635 A1 | 9/1996 |
| EP | 0 831 098 B1 | 11/2001 |
| WO | WO 02/18390 A1 | 3/2002 |
| WO | WO 03/055438 A2 | 7/2003 |
| WO | WO 03/097650 A1 | 11/2003 |
| WO | WO 03/101997 A1 | 12/2003 |
| WO | WO 2004/006933 A2 | 1/2004 |

*Primary Examiner*—Brenda L Coleman
(74) *Attorney, Agent, or Firm*—Cozen O'Connor (57) ABSTRACT

Said mixed solvate is a solvate of olanzapine/water/tetrahydrofuran in the proportion 1:1:1/2 (I). The method for preparing said solvate comprises treating a crude anhydrous olanzapine with a mixture of tetrahydrofuran/water. The method for preparing Form I of olanzapine includes desolvating the mixed solvate of formula I, by means of drying, in vacuo and under temperature-controlled conditions.

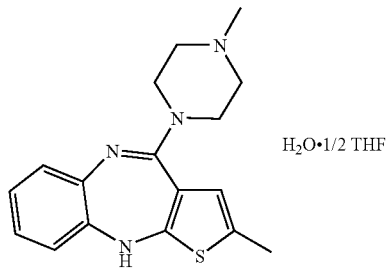

14 Claims, 7 Drawing Sheets

MIXED SOLVATE OF OLANZAPINE, METHOD FOR PREPARING IT AND METHOD FOR PREPARING FORM I OF OLANZAPINE THEREFROM

This application is a national stage entry application under 35U.S.C. 371 of PCT/IB05/02209, filed Jul. 7, 2005.

FIELD OF THE INVENTION

The present invention relates to a new mixed solvate of olanzapine. In particular, the present invention relates to a mixed solvate of olanzapine/water/tetrahydrofuran in a proportion of 1:1:1/2.

The present invention also relates to a method for preparing said mixed solvate together with a method for preparing Form I of olanzapine front said solvate.

BACKGROUND OF THE INVENTION

Olanzapine is a thienobenzodiazepine of formula (I):

that acts as an antagonist on receptors of dopamine D1, D2, D3, D4 and D5; of serotonine 5-HT2 and 5HT3; alpha-1-adrenergics, collinergics and H1 histaminergics.

Olanzapine was disclosed for the first time in patent EP0454436B1, in which said thienobenzodiazepine was prepared from 4-amino-2-methyl-10H-thieno [2,3-b] [1,5]benzodiazepine and N-methyipiperazine in DMSO/toluene, followed by isolation of the olanzapine by addition of water and crystallisation with acetonitrile.

Patent EP0733635A1 discloses two polymorphic forms of olanzapine: Form I (metastable) and Form II (stable), Form I being that obtained in the first patent EP0454436B1.

The metastable character of Form I relates to a change of colour under ambient storage conditions.

Patents EP0733634A1, U.S. Pat. No. 5,703,232 and EP0831098A2 claim the preparation of hydrated species and of solvates from olanzapine alcohols and the use thereof for preparing Form II (stable) of olanzapine, although in U.S. Pat. No. 5,703,232 the stable form is called Form I (while in the other documents the stable form is referred to as Form II).

U.S. Pat. No. 5,637,584 claims the solvate of dichloromethane of olanzapine and a method for preparing it.

Finally, patents WO0218390A1, WO03097650A1, WO03055438A2, WO03101997 and WO2004006933A2 claim the preparation of Form I olanzapine. In patent WO0218390A1 Form I of olanzapine is prepared from the dihydrate I, from the monohydrate I or from Form II, by crystallisation in dichloromethane. In patent WO03097650A1, Form I is prepared by extraction and subsequent purification with dichloromethane of olanzapine prepared by condensation of 4-amino-2-methyl-10H-thieno [2,3-b] [1,5]benzodiazepine and N-methylpiparazine. Said patent claims a mixed solvate of dichloromethane/water and a mixed solvate of DMSO/water. In patent WO03055438A2. Form I is prepared by successive crystallisations and decolourations in C1-C4 alcohols. In patent WO03101997, Form I is prepared by precipitation from a mixture of an organic solvent in a basic medium such as toluene and methanolic soda, seeding with Form I itself. In WO2004006933A2, Form I is prepared by crystallisation of a mixture of solvents that contain IPA. In some of the preceding patents, the Form I obtained is described as stable to colour changes.

DESCRIPTION OF THE INVENTION

The object of the present invention is to provide a new mixed solvate of olanzapine together with methods for preparing it.

A first aspect of the present invention is therefore to provide a mixed solvate of olanzapine/water/tetrahydrofuran in the proportion 1:1:1/2 (I):

A second aspect of the present invention is to provide a method for preparing a solvate in accordance with the first aspect of the invention. Said solvate can be prepared from the crude anhydrous olanzapine prepared by methods known by a man skill in the art (such as the methods described in patent EP0454436B1) by treating it with a mixture of tetrahydrofuran/water.

In one embodiment of the second aspect of the invention, said mixed solvate of formula I is prepared by treating the residue obtained from condensation of 4-amino-2-methyl-10H-thieno[2,3-b] [1,5]benzodiazepine hydrochloride with N-methylpiperazine directly with a tetrahydrofuran/water mixture, without need to isolate the crude olanzapine.

A third aspect of the present invention is to provide a method for preparing Form I of olanzapine from a solvate, of formula I, according to the first aspect of the present invention. Said method comprises desolvating the mixed solvate of formula I, by means of drying, in vacuo and under temperature-controlled conditions, providing a Form I olanzapine that remains stable and without undergoing colour changes under ambient storage conditions, which makes it suitable for pharmaceutical formulation.

DESCRIPTION OF THE FIGURES

FIG. 3 DSC of the mixed solvate of olanzapine/water/tetrahydrofuran in the proportion 1:1:1/2. Mettler-Toledo model DSC821e thermal analysis equipment was used, at a heating rate of 10° C./min in open capsule and with a nitrogen flow of 50 mL/min. In this spectrum a loss of tetrahydrofuran and water is first observed (70-110° C. range) and a subsequent fusion peak at 195° C.

FIG. 4 TGA of the mixed solvate of olanzapine/water/tetrahydrofuran in the proportion 1:1:1/2.—Mettler-Toledo model TG50 thermal analysis equipment was used, at a heating rate of 10° C./min in open capsule and with a nitrogen flow of 50 mL/min. The spectrum shows a 14.7% weight loss.

DETAILED DESCRIPTION OF THE INVENTION

The new mixed solvate object of the present invention is identified by its powder X-ray diffraction pattern.

Figure 4:
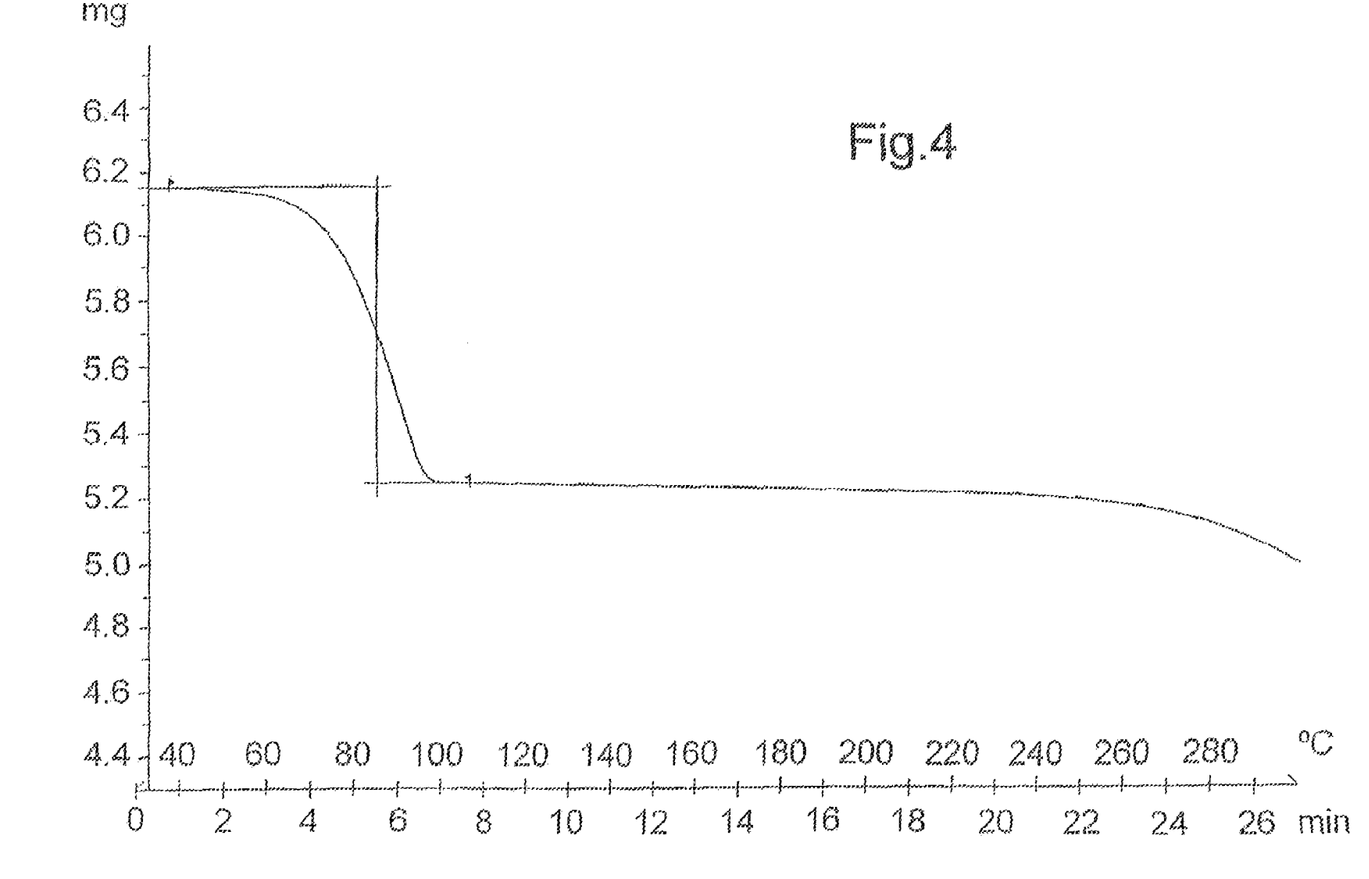

The composition of the mixed solvate, to which the first aspect of the invention relates, is established from the TGA (FIG. 4), with a loss of 14.7-14.8% observed owing to the sum of tetrahydrofaran and water, and by means of Karl Fischer water determination, showing 4.8-4.9% of water. It is determined from these values that the olanzapine/water/tetrahydrofuran solvate retains the proportion 1:1:1/2.

Figure 1:
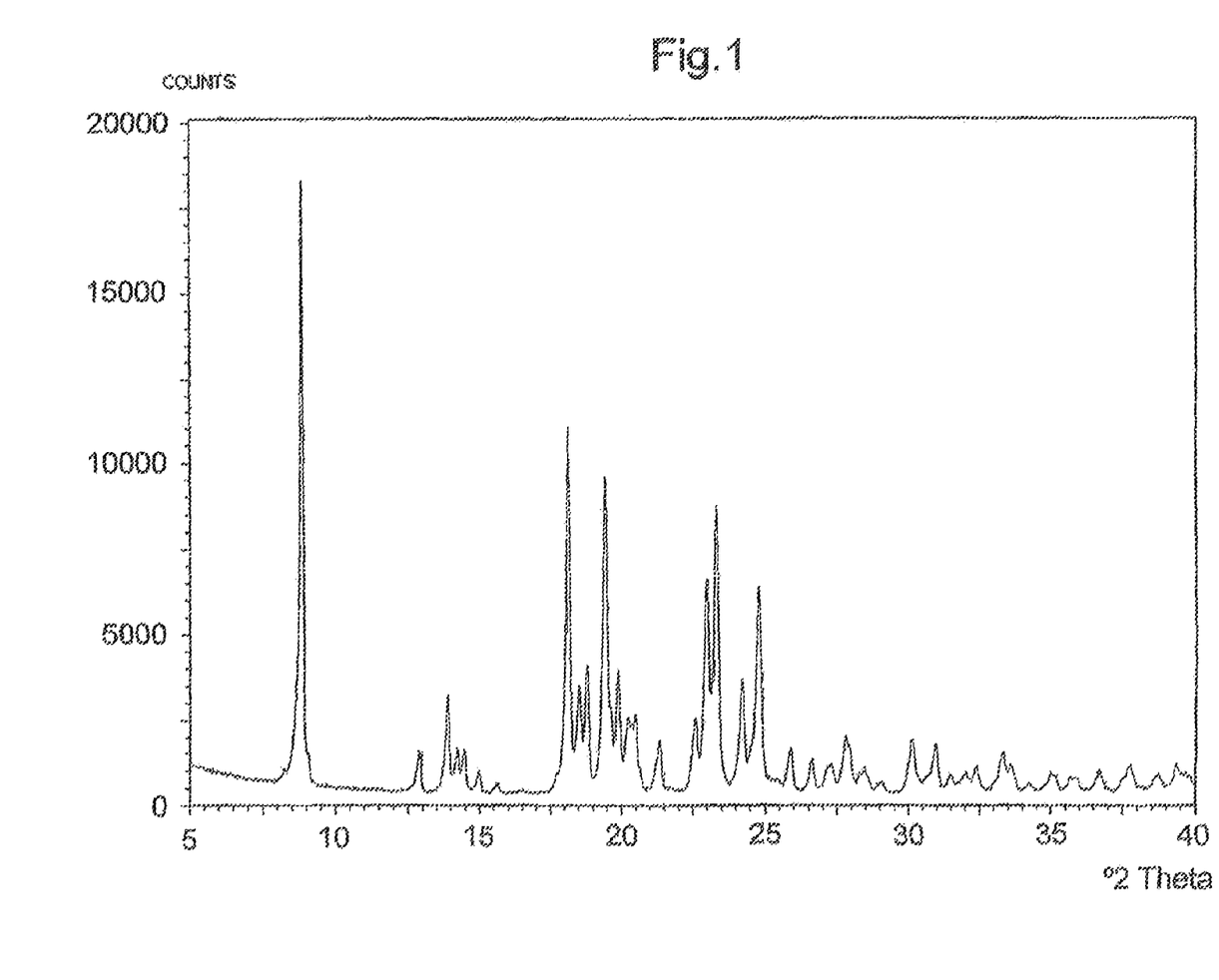
FIG. 1 X-ray diffraction pattern of the mixed solvate of olanzapine/water/tetrahydrofuran in the proportion 1:1:1/2 (vertical axis: height (counts); horizontal axis: angle °2θ)
Figure 2:
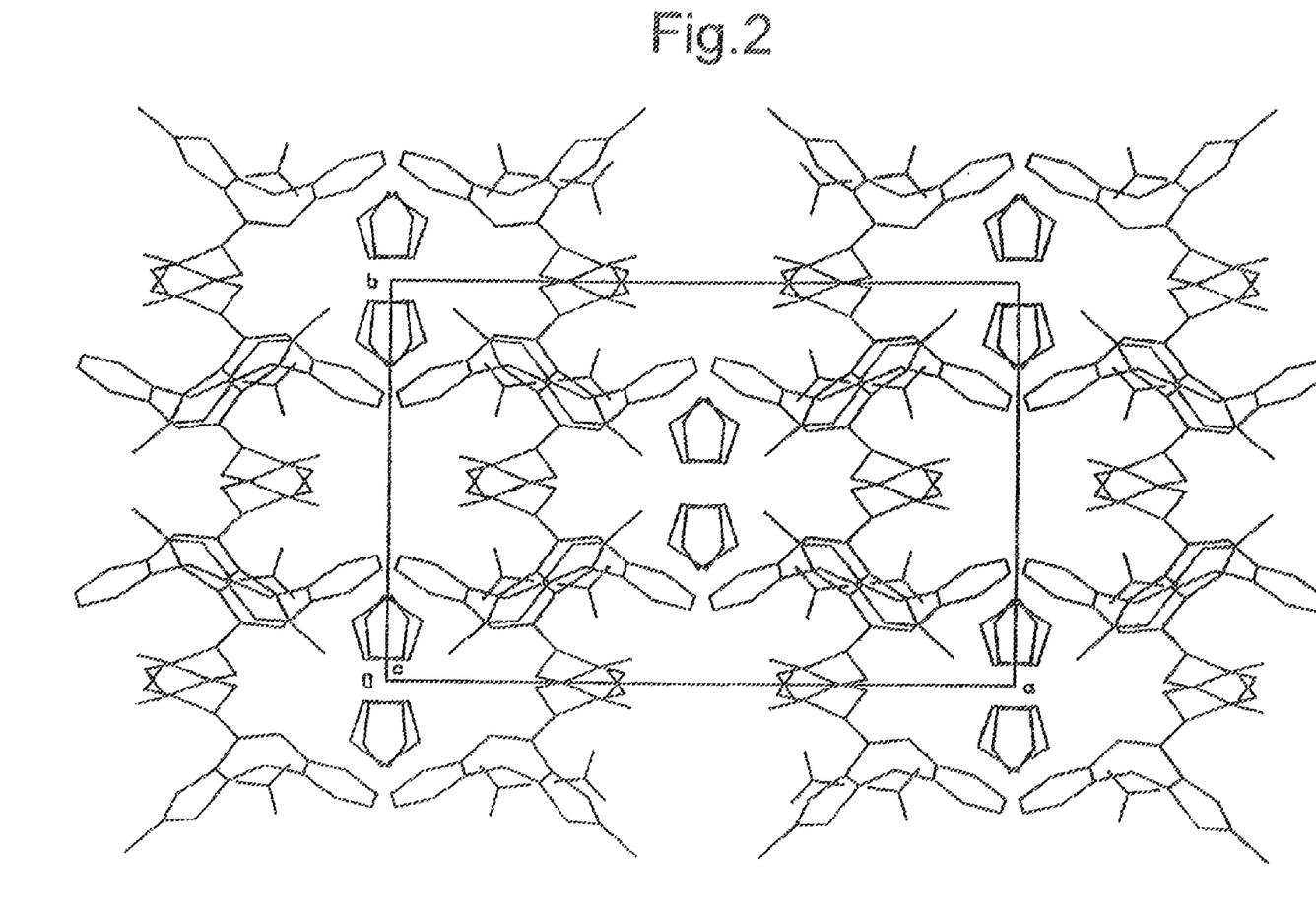
FIG. 2 Monocrystal structure of the mixed solvate of olanzapine/water/tetrahydrofuran in the proportion 1:1:1/2. An Enraf Nonius CAD4 automatic diffractometer was used. It was irradiated with Kα radiation of Mo (λ=0.71069 Å) obtained with graphite monochromator. It is observed that the elementary cell of the mixed solvate contains 8 molecules of olanzapine, 8 molecules of water and 4 molecules of tetrahydrofuran, which means that the olanzapine/water/tetrahydrofuran mixed solvate retains the proportion 1:1:1/2.
Figure 3:
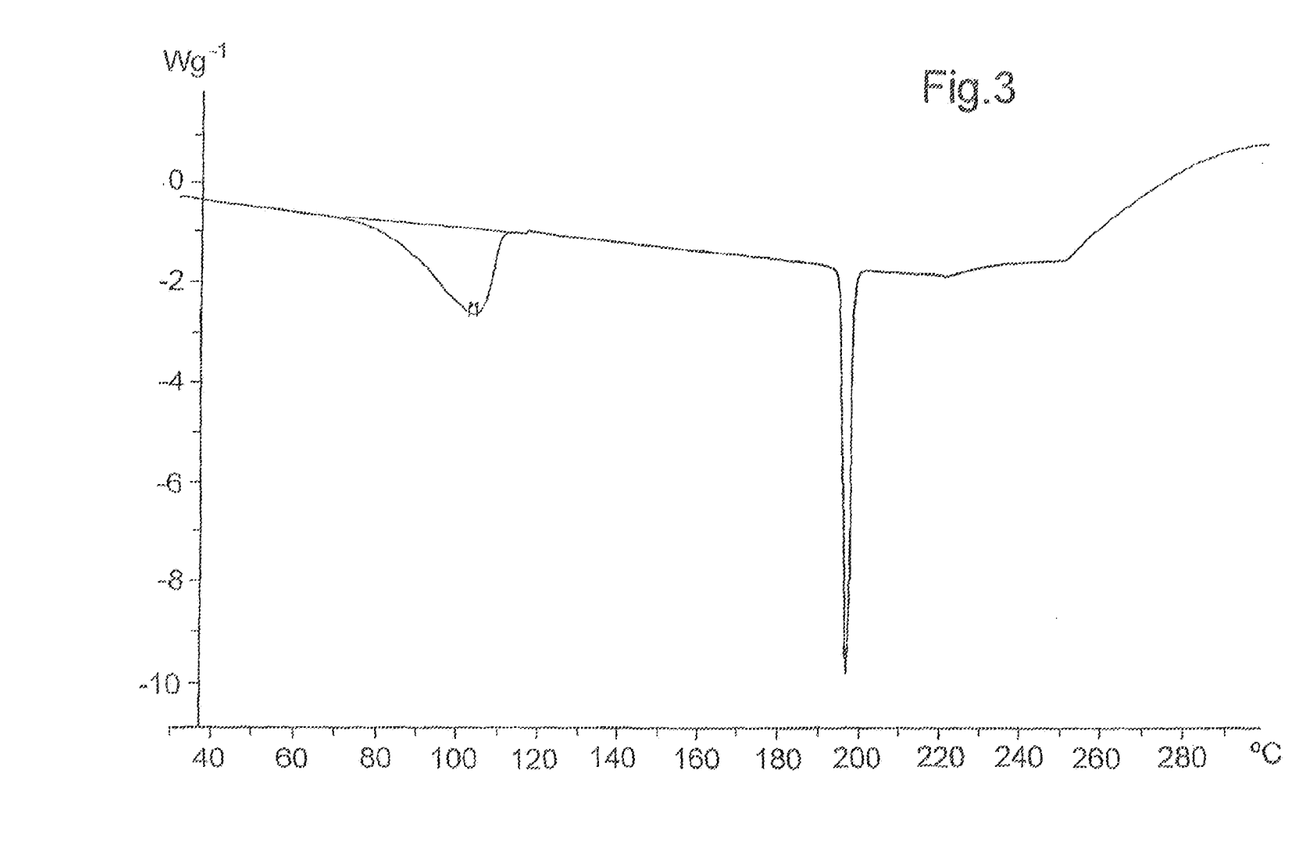

Said composition is further confirmed by integration of the tetrahydrofuran signals in the NMR spectrum of $^1$H (FIG. 5) and by the monocrystal crystalline structure determined by X-rays (FIG. 2).

Table 1 shows the peaks observed in an X-ray diffraction pattern using a PHILIPS X'Pert automatic diffractometer for crystalline powder provided with a Cu tube and graphite secondary monochromator (KαCu wavelength, 1.5419 Å).

The X-ray diffraction pattern of the solvate is characterised by the position (°2θ), the interplanar spacing d and the relative intensities $I/I_0$. Said diffraction pattern reveals the following characteristic peaks of said mixed solvate:

TABLE 1

| Position(°2θ) | d (m$^{-10}$) | $I/I_0$ |
|---|---|---|
| 8.83 | 10.010 | 100 |
| 9.05 | 9.777 | 5 |
| 12.87 | 6.879 | 7 |
| 13.87 | 6.383 | 16 |
| 14.19 | 6.243 | 7 |
| 14.43 | 6.140 | 7 |
| 14.97 | 5.920 | 4 |
| 18.12 | 4.896 | 61 |
| 18.50 | 4.795 | 18 |

TABLE 1-continued

| Position(°2θ) | d (m$^{-10}$) | $I/I_0$ |
|---|---|---|
| 18.77 | 4.727 | 21 |
| 19.43 | 4.570 | 53 |
| 19.62 | 4.525 | 14 |
| 19.88 | 4.467 | 20 |
| 20.20 | 4.396 | 13 |
| 20.46 | 4.341 | 13 |
| 21.33 | 4.166 | 9 |
| 22.58 | 3.938 | 12 |
| 22.98 | 3.870 | 35 |
| 23.31 | 3.817 | 48 |
| 24.23 | 3.674 | 19 |
| 24.79 | 3.592 | 35 |
| 25.89 | 3.441 | 7 |
| 26.61 | 3.350 | 5 |
| 27.17 | 3.282 | 4 |
| 27.29 | 3.268 | 4 |
| 27.79 | 3.211 | 10 |
| 27.94 | 3.194 | 7 |
| 28.46 | 3.136 | 4 |
| 30.11 | 2.968 | 9 |
| 30.95 | 2.890 | 8 |
| 32.38 | 2.765 | 4 |
| 33.31 | 2.689 | 7 |
| 33.59 | 2.668 | 5 |
| 37.75 | 2.383 | 4 |
| 39.35 | 2.290 | 5 |

Figure 6:
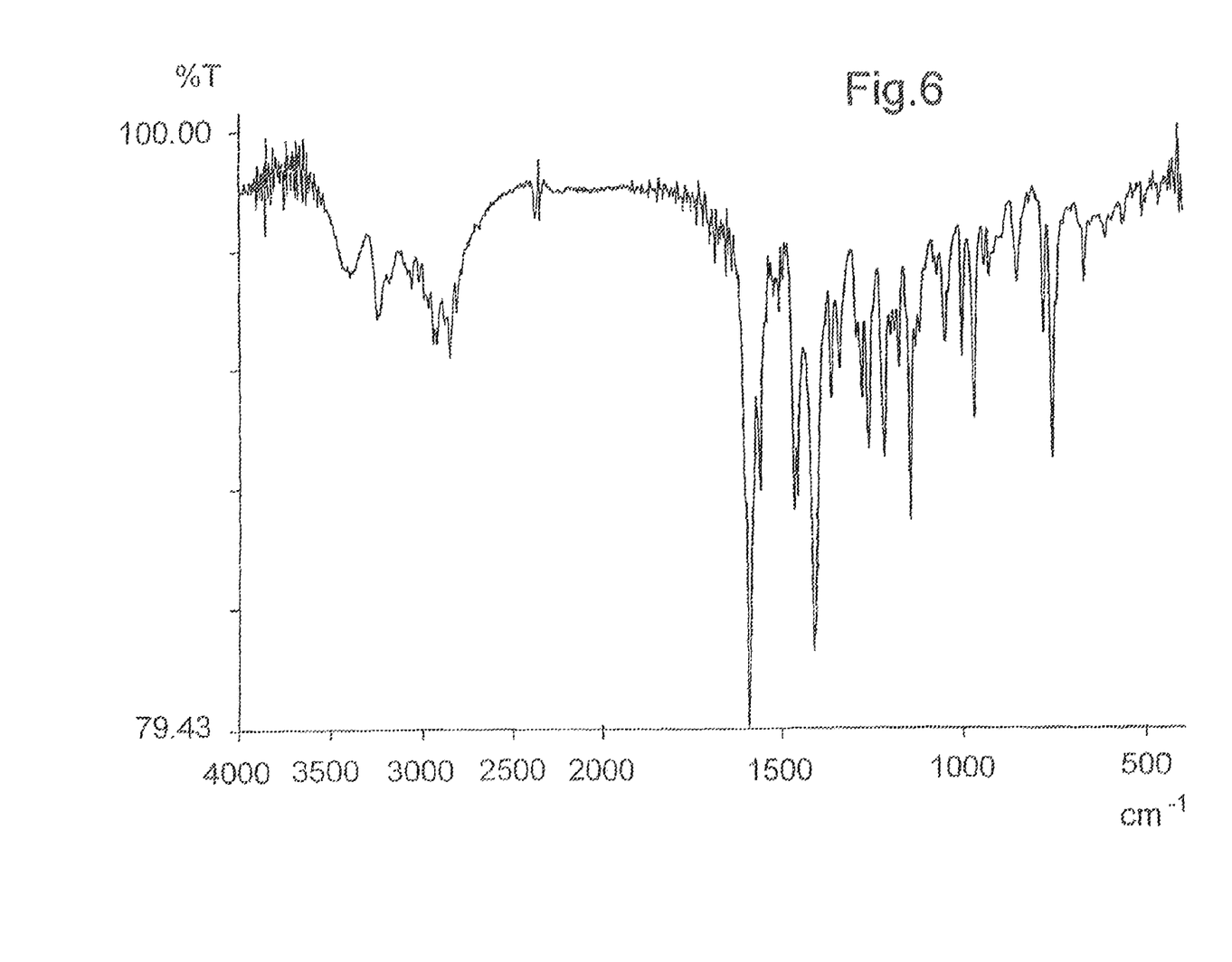
FIG. 6 Infrared spectrum of the mixed solvate of olanzapine/water/fetrahydrofuran in proportion 1:1:1/2. It was carried out on KBr tablet, using a Perkin Elmer FTIR 1600 appliance.
Figure 7:
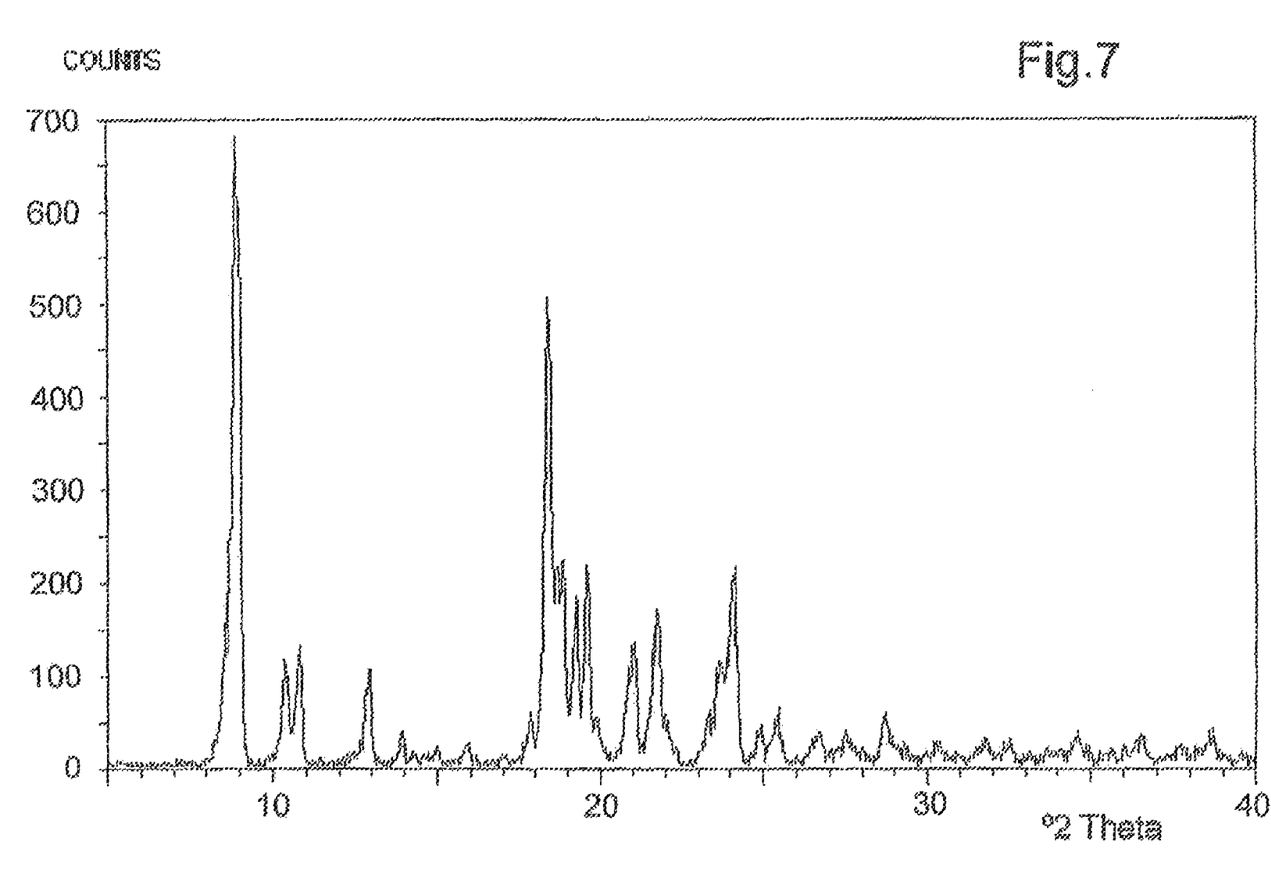
FIG. 7 X-ray diffraction pattern of Form I of olanzapine prepared according to Example 3. (vertical axis: height (counts); horizontal axis: angle °2θ)

In one embodiment of the first aspect of the invention, said mixed solvate of olanzapine/water/tetrahydrofuran has absorptions in an IR spectrum recorded on KBr tablet at the following wavelengths (cm$^{-1}$): 3390, 3240, 2930, 2830, 1595, 1560, 1465, 1410, 1270, 1220, 1140, 965, 755. (FIG. 6).

A second aspect of the present, invention is to provide a method for preparing a mixed solvate of olanzapine/water/tetrahydrofuran in the proportion 1:1:1/2 in accordance with the first aspect of the invention.

Said solvate can be prepared by solvating the crude anhydrous olanzapine (prepared according to known methods such as those described in patent EP0454436B1) in a mixture of tetrahydrofuran/water in a proportion between 1:10 and 10:1 v/v, preferably between 1:5 and 5:1 v/v at a temperature of between 20 and 80° C., preferably between 40 and 60° C.

Optionally, said solvate can be prepared directly without need to isolate the crude anhydrous olanzapine, simply, with high purity and without the use of toxic solvents, starting from condensation of the 4-amino-2-methyl-10H-thieno[2,3-b][1,5]benzodiazepine hydrochloride (II) with N-methylpiperazine (III).

This condensation is carried out without solvent, using an excess of N-methylpiperazine of 4 to 12 equivalents, preferably of 6 to 8 equivalents, at a temperature between 100° C. and 145° C., maintaining a slight current or bubbling of nitrogen to displace the ammonia generated in the reaction.

Once the reaction has finished, the excess N-methylpiperazine is recovered by means of distillation and the resulting crude product is treated with a mixture of tetrahydrofuran/water in a proportion of between 1:10 and 10:1 v/v, preferably between 1:5 and 5:1 v/v, precipitating the mixed solvate of olanzapine/water/tetrahydrofuran in the proportion 1:1:1/2.

The mixed solvate obtained can be purified by means of simple techniques, such as recrystallisation or washing with a mixture of tetrahydrofuran/water at a temperature of between 20 and 80° C., preferably between 40 and 60° C., to give a solvate of high purity by HPLC, with less than 0.3% of total impurities.

Advantageously, in the method in accordance with the second aspect no toxic solvents are used to prepare the solvate of olanzapine from 4-amino-2-methyl-10H-thieno[2,3-b][1,5]benzodiazepine and N-methylpiperazine.

A third aspect of the present invention is a method for preparing Form I olanzapine from the mixed solvate of olanzapine/water/tetrahydrofuran in the proportion 1:1:1/2. Said method comprises drying the solvate in vacuo at a pressure that ranges between 1 and 40 mmHg, preferably between 1 and 20 mmHg, and at a temperature controlled between 10 and 50° C., preferably between 20 and 40° C.

The method according to the third aspect of the invention is simple, and permits the end product (Form I olanzapine) to be obtained with a high chemical purity (as determined by HPLC, the level of total impurities is lower than 0.3% and high polymorphic purity (Form II<2%). Said Form I remains stable and shows no colour variation under ambient storage conditions.

In one embodiment of the third aspect of the present invention, the solid (mixed solvate) is maintained under stirring during the drying procedure, in order to encourage the desolvating process and to minimise the drying time.

The X-ray diffraction pattern of Form I obtained according to the method of the invention, is characterised by the position (°2θ), the interplanar spacing d and relative $I/I_0$ intensities (Table 2).

TABLE 2

| Position(°2θ) | d (m$^{-10}$) | $I/I_0$ |
|---|---|---|
| 8.885 | 9.944 | 100 |
| 9.005 | 9.812 | 86 |
| 10.395 | 8.503 | 14 |
| 10.815 | 8.174 | 20 |
| 12.915 | 6.850 | 16 |
| 13.915 | 6.359 | 4 |
| 17.830 | 4.971 | 8 |
| 18.385 | 4.822 | 75 |
| 18.785 | 4.720 | 32 |
| 19.230 | 4.612 | 27 |
| 19.620 | 4.521 | 29 |
| 21.050 | 4.217 | 19 |
| 21.770 | 4.079 | 24 |
| 23.635 | 3.761 | 16 |
| 24.095 | 3.691 | 30 |
| 24.865 | 3.578 | 6 |
| 25.465 | 3.495 | 9 |
| 26.690 | 3.337 | 5 |
| 27.515 | 3.239 | 5 |
| 28.665 | 3.112 | 8 |
| 34.580 | 2.592 | 5 |
| 36.525 | 2.458 | 4 |
| 38.645 | 2.328 | 4 |

EXAMPLES

Example 1

A mixture consisting of 50 g (0.188 moles) of 4-amino-2-methyl-10H-thieno[2,3-b][1,5]benzodiazepine hydrochloride and 125 mL (1.127 moles) of N-methylpiperazine is heated at reflux (interior temperature 140° C.), maintaining a slight current of nitrogen. Once two hours have elapsed the reaction terminates, and the mixture is cooled to 70° C. 40 mL de N-methylpiperazine is then distilled at 70° C. in vacuo (40 mmHg), and 125 mL of a tetrahydrofuran/water 1:4 (v/v) mixture is added. The mixture is kept under stirring for 15 min at 70° C., is cooled to 20-25° C. and left at this temperature for one hour. The mixture is filtered and the solid is washed with 50 mL of tetrahydrofuran/water 1:4 (v/v) mixture and twice with 100 mL of water. The solid obtained is dried in an air oven at 42° C. to constant weight, yielding 65.1 g (94.4%) of the mixed solvate of olanzapine/water/tetrahydrofuran in the proportion 1:1:1/2.

25 g of the olanzapine solvate obtained is purified, with 100 mL of THF and 25 mL of water by heating the mixture at 50° C. for 15 min. After cooling to 20-25° C. for one hour, and then to 0° C. over a further hour, the solid is filtered and dried in an air oven at 42° C. to constant weight, yielding 21.8 g of mixed solvate of olanzapine/water/tetrahydrofuran in the proportion 1:1:1/2 with less than 0.3% of total impurities by HPLC.

Loss by drying (determination by TGA): 14.7%

Determination of water (KF): 4.9%

Figure 5:
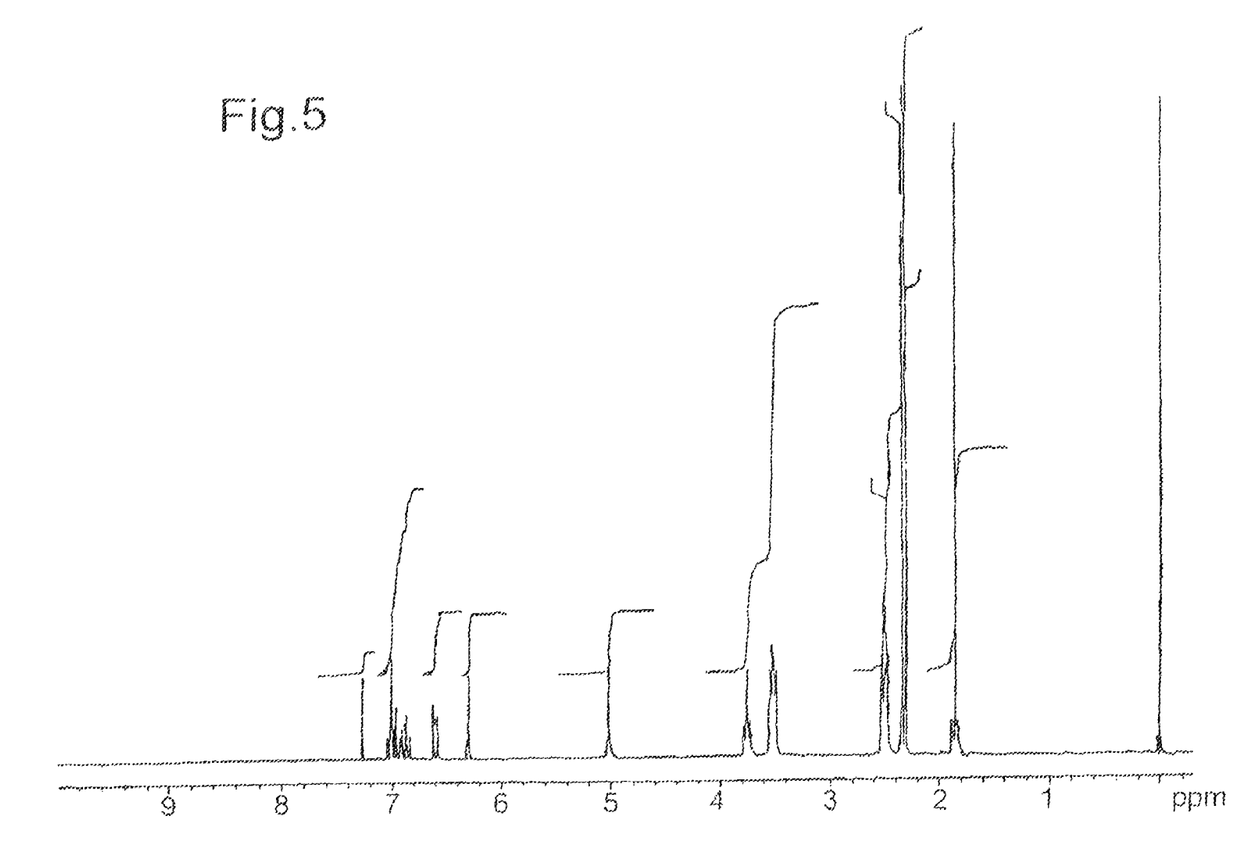
FIG. 5 NMR spectrum of $^1$H (CDCl$_3$) of the mixed solvate of olanzapine/water/tetrahydrofuran in the proportion 1:1:1/2.—Varian Gemini 200 equipment was used. The relative integration of the signals of tetrahydrofuran (3.75 ppm, 4 H) and the protons of the symmetrical methylenes of the piperazine ring of the olanzapine (3.50 ppm, 4H) correspond to the olanzapine/tetrahydrofuran molar ratio of 1:1/2.

Molar ratio between olanzapine/tetrahydrofuran of 1:1/2 confirmed by NMR of $^1$H (FIG. 5).

Example 2

A mixture made up of 100 mL of THF, 25 mL of water and 25 g of crude anhydrous olanzapine obtained by following the method described in patent EP0454436B1 is heated for 30 min at 50° C. After cooling first to 20-25° C. for one hour and then to 0° C. over a further hour, the solid is filtered and dried in an air oven at 42° C. to constant weight, yielding 24.9 g (85%) of mixed solvate of olanzapine/water/tetrahydrofuran in the proportion 1:1:1/2.

Example 3

(1) 1 g of the mixed solvate of olanzapine/water/tetrahydrofuran in the proportion 1:1:1/2 is dried under oil pump vacuum (1 mmHg) for 4-5 h until no sign of tetrahydrofuran is observed by NMR $^1$H. The solid obtained presents the characteristic X-ray diffraction pattern of Form I of olanzapine. M.p. 195° C.

(2) 20 g of the mixed solvate of olanzapine/water/tetrahydrofuran in the proportion 1:1:1/2 is dried at 20 mmHg of vacuum under mechanical stirring and applying an external bath at 40° C. for 10 h. By NMR $^1$H, DSC and TGA it is observed that no remains of tetrahydrofuran and water are left. The solid obtained presents the characteristic X-ray diffraction pattern of Form I of olanzapine. M.p. 195° C.

The invention claimed is:

1. Mixed solvate of olanzapine/water/tetrahydrofuran in a proportion of 1:1:1/2 of formula (I);

·H₂O ·½ THF.

I

2. Mixed solvate according to claim 1, comprising the following position (°2θ), interplanar spacing d and relative intensities I/I₀ in the X-ray diffraction pattern:

| Position(°2θ) | d (m⁻¹⁰) | I/I₀ |
|---|---|---|
| 8.83 | 10.010 | 100 |
| 9.05 | 9.777 | 5 |
| 12.87 | 6.879 | 7 |
| 13.87 | 6.383 | 16 |
| 14.19 | 6.243 | 7 |
| 14.43 | 6.140 | 7 |
| 14.97 | 5.920 | 4 |
| 18.12 | 4.896 | 61 |
| 18.50 | 4.795 | 18 |
| 18.77 | 4.727 | 21 |
| 19.43 | 4.570 | 53 |
| 19.62 | 4.525 | 14 |
| 19.88 | 4.467 | 20 |
| 20.20 | 4.396 | 13 |
| 20.46 | 4.341 | 13 |
| 21.33 | 4.166 | 9 |
| 22.58 | 3.938 | 12 |
| 22.98 | 3.870 | 35 |
| 23.31 | 3.817 | 48 |
| 24.23 | 3.674 | 19 |
| 24.79 | 3.592 | 35 |
| 25.89 | 3.441 | 7 |
| 26.61 | 3.350 | 5 |
| 27.17 | 3.282 | 4 |
| 27.29 | 3.268 | 4 |
| 27.79 | 3.211 | 10 |
| 27.94 | 3.194 | 7 |
| 28.46 | 3.136 | 4 |
| 30.11 | 2.968 | 9 |
| 30.95 | 2.890 | 8 |
| 32.38 | 2.765 | 4 |
| 33.31 | 2.689 | 7 |
| 33.59 | 2.668 | 5 |
| 37.75 | 2.383 | 4 |
| 39.35 | 2.290 | 5. |

3. Solvate according to claim 1, wherein it has absorptions in an IR spectrum recorded on KBr tablet at the following wavelengths(cm⁻¹): 3390, 3240, 2930, 2830, 1595, 1560, 1465, 1410, 1270, 1220, 1140, 965, 755.

4. Method for preparing a mixed solvate according to claim 1, wherein it comprises solvating a crude anhydrous olanzapine with a mixture of tetrahydrofuran/water in a proportion between 1:10 and 10:1 v/v at a temperature ranging between 20 and 80° C.

5. Method according to claim 4, wherein said temperature ranges between 40 and 60° C.

6. Method according to claim 4, wherein said proportion of tetrahydrofuran/water ranges between 1:5 and 5:1 v/v.

7. Method for preparing a mixed solvate according to claim 1, wherein said mixed solvate of olanzapine is prepared by undertaking the following stages:
 a) condensation of a compound of formula II with a compound of formula III:

II  III in the presence of any excess of N-methylpiperazine that ranges between 4 and 12 equivalents, at a temperature that ranges between 100-145° C. and under nitrogen atmosphere;
 b) distillation of the resulting mixture; and
 c) mixing the resulting crude product from stage (b) with tetrahydrofuran and water in a proportion between 1:10 and 10:1 v/v, when precipitation of said mixed solvate of olanzapine occurs.

8. Method according to claim 7, wherein in said stage c) the proportion of tetrahydrofuran and water is between 1:5 and 5:1 v/v.

9. Method according to claim 7, wherein the precipitate obtained in stage c) is purified.

10. Method according to claim 7, wherein said excess of N-methylpiperazine ranges between 6 and 8 equivalents.

11. Method for preparing Form I of olanzapine that comprises drying a mixed tetrahydrofuran and H₂O solvate of olanzapine according to claim 1 in vacuo at a pressure ranging between 1 and 40 mmHg and at a temperature that ranges between 10 and 50° C.

12. Method according to claim 11, wherein said pressure ranges between 1 and 20 mmHg.

13. Method according to claim 12, wherein said temperature ranges between 20 and 40° C.

14. Method according to claim 11, wherein said solvate is maintained under stirring during the drying procedure.

* * * * *